US009682027B2

(12) United States Patent
Prencipe et al.

(10) Patent No.: US 9,682,027 B2
(45) Date of Patent: *Jun. 20, 2017

(54) ORAL CARE PRODUCT AND METHODS OF USE AND MANUFACTURE THEREOF

(75) Inventors: Michael Prencipe, Windsor, NJ (US); Diane Cummins, Livingston, NJ (US); Richard Scott Robinson, Belle Mead, NJ (US); Sarita V. Mello, Somerset, NJ (US); Richard J. Sullivan, Atlantic Highlands, NJ (US); Suman Chopra, Monroe, NJ (US); Karen J. DePierro, Piscataway, NJ (US); Lynette Zaidel, Cranford, NJ (US); Constantina Christopoulou, Somerset, NJ (US); Ravi Subramanyam, Belle Mead, NJ (US); Donghui Wu, Bridgewater, NJ (US); Andre M. Morgan, Robbinsville, NJ (US); Ralph Peter Santarpia, III, Edison, NJ (US); Qin Wang, Monmouth Junction, NJ (US); Gary Edward Tambs, Belle Mead, NJ (US); Rajnish Kohli, Hillsborough, NJ (US); Virginia Monsul Barnes, Ringoes, NJ (US); Sergio Leite, Kendall Park, NJ (US); Eric A. Simon, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 2585 days.

This patent is subject to a terminal disclaimer.

(21) Appl. No.: 12/058,424

(22) Filed: Mar. 28, 2008

(65) Prior Publication Data

US 2009/0202451 A1  Aug. 13, 2009

Related U.S. Application Data

(60) Provisional application No. 61/027,431, filed on Feb. 8, 2008, provisional application No. 61/027,420, filed on Feb. 8, 2008, provisional application No. 61/027,435, filed on Feb. 8, 2008, provisional application No. 61/027,432, filed on Feb. 8, 2008.

(51) Int. Cl.

| A61K 8/00 | (2006.01) |
|---|---|
| A61Q 11/00 | (2006.01) |
| A61K 8/21 | (2006.01) |
| A61K 8/25 | (2006.01) |
| A61K 8/19 | (2006.01) |
| A61K 8/40 | (2006.01) |
| A61K 8/44 | (2006.01) |
| A61K 31/198 | (2006.01) |

(52) U.S. Cl.
CPC .................. *A61K 8/44* (2013.01); *A61K 8/25* (2013.01); *A61K 31/198* (2013.01); *A61Q 11/00* (2013.01)

(58) Field of Classification Search
USPC .............................. 424/49, 52, 54, 682, 687
See application file for complete search history.

(56) References Cited

U.S. PATENT DOCUMENTS

| 3,925,543 A | 12/1975 | Donohue |
|---|---|---|
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,110,083 A * | 8/1978 | Benedict ..................... 51/295 |
| 4,146,607 A | 3/1979 | Ritchey |
| 4,154,813 A | 5/1979 | Kleinberg |
| 4,160,821 A | 7/1979 | Sipos |
| 4,213,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg |
| 4,466,954 A | 8/1984 | Ichikawa et al. |
| 4,528,181 A | 7/1985 | Morton et al. |
| 4,532,124 A | 7/1985 | Pearce |

(Continued)

FOREIGN PATENT DOCUMENTS

| EP | 0 549 281 A | 6/1993 |
|---|---|---|
| JP | H09-295924 | 11/1987 |

(Continued)

OTHER PUBLICATIONS

Machado et al., "CaviStat Confection Inhibition of Caries in Posterior Teeth," 83rd Session of the American Association for Dental Research, Mar. 21-24, 2007, Abstract, New Orleans Louisiana.
Chatterjee etal., "Bacterial Acidification and CaviStat Alkalinization of Occlusal Fissure pH," 83rd Session of the American Association for Dental Research, Mar. 9-12, 2005, Baltimore, MDal.
Kleinberg, I., "A Mixed-Bacteria Ecological Apporach to Understanding the Role of the Oral Bacteria in Dental Caries Causation: An Alternative to *Streptococcus* Mutans and the Specific-Plaque Hypothesis," Crit. Rev. Oral Biol. Med., (2002) pp. 108-125 12:2.
Kleinberg, I., "A New Saliva-Based Anticaries Composition," Dentistry Today, Feb. 1999 18:2.

(Continued)

*Primary Examiner* — Lezah Roberts

(57) ABSTRACT

This invention relates to oral care compositions comprising a basic amino acid or salt thereof, and a small particle fraction: and to methods of using and of making these compositions.

48 Claims, No Drawings

(56) References Cited

U.S. PATENT DOCUMENTS

| | | | |
|---|---|---|---|
| 4,538,990 | A | 9/1985 | Pashley |
| 4,645,662 | A | 2/1987 | Nakashima et al. |
| 4,656,031 | A | 4/1987 | Lane et al. |
| 4,725,576 | A | 2/1988 | Pollock et al. |
| 4,992,258 | A | 2/1991 | Mason |
| 4,997,640 | A | 3/1991 | Bird et al. |
| 5,032,386 | A * | 7/1991 | Gaffar et al. .............. 424/49 |
| 5,096,700 | A | 3/1992 | Siebel et al. |
| 5,286,480 | A | 2/1994 | Boggs et al. |
| 5,334,617 | A | 8/1994 | Ulrich et al. |
| 5,370,865 | A | 12/1994 | Yamagishi et al. |
| 5,639,795 | A | 6/1997 | Friedman et al. |
| 5,747,004 | A | 5/1998 | Giani et al. |
| 5,762,911 | A | 6/1998 | Kleinberg et al. |
| 5,906,811 | A | 5/1999 | Hersh |
| 5,922,346 | A | 7/1999 | Hersh |
| 5,997,301 | A | 12/1999 | Linden |
| 6,217,851 | B1 | 4/2001 | Kleinberg et al. |
| 6,436,370 | B1 | 8/2002 | Kleinberg et al. |
| 6,488,961 | B1 | 12/2002 | Robinson et al. |
| 6,524,558 | B2 | 2/2003 | Kleinberg et al. |
| 6,558,654 | B2 | 5/2003 | McLaughlin |
| 6,805,883 | B2 | 10/2004 | Chevaux et al. |
| 2002/0037258 | A1 | 3/2002 | Dodd et al. |
| 2002/0064504 | A1* | 5/2002 | Kleinberg et al. .............. 424/49 |
| 2002/0081360 | A1 | 6/2002 | Burgard et al. |
| 2003/0133885 | A1 | 7/2003 | Kleinberg et al. |
| 2007/0258916 | A1 | 11/2007 | Ferracane et al. |

FOREIGN PATENT DOCUMENTS

| | | |
|---|---|---|
| JP | H6-92860 | 4/1994 |
| JP | 06-271437 | 9/1994 |
| JP | 08-175943 | 7/1996 |
| JP | H10-17449 | 1/1998 |
| JP | 2001-504083 | 3/2001 |
| JP | 2008-544940 | 12/2008 |
| RU | 2163798 | 3/2001 |
| WO | 9325183 A | 12/1993 |
| WO | WO 02/085319 | 10/2002 |
| WO | 2007011552 A | 1/2007 |
| WO | 2007068916 A | 6/2007 |

OTHER PUBLICATIONS

Packaging with ingredient list for DenClude (launched Dec. 2004).
Packaging with ingredient list for ProClude (launched Jul. 2002).
International Search Report PCT/US2008/058679 Dated Jan. 5, 2009.
"Immunization", The Great Vocabulary of Medicinal Terms, Compiler Fedotov V.D., M. Zao Zentpoligraf, 2007, p. 340, right column.
Stober W. et al., "Controlled Growth of Monodisperse Silica Spheres in the Micron Size Range," Journal of Colloid and Interface Science, 1968, 26, pp. 62-69.

* cited by examiner

ORAL CARE PRODUCT AND METHODS OF USE AND MANUFACTURE THEREOF

This application claims the benefit of U.S. Ser. No. 61/027,435 filed Feb. 8, 2008, U.S. Ser. No. 61/027,431 filed Feb. 8, 2008, U.S. Ser. No. 61/027,432 filed Feb. 8, 2008 and U.S. Ser. No. 61/027,420 filed Feb. 8, 2008, the contents of which are incorporated herein by reference.

FIELD OF THE INVENTION

This invention relates to oral care compositions comprising small particles together with a basic amino acid or salt thereof, and to methods of using and of making these compositions.

BACKGROUND OF THE INVENTION

Arginine and other basic amino acids have been proposed for use in oral care and are believed to have significant benefits in combating cavity formation and tooth sensitivity. Commercially available arginine-based toothpaste, such as ProClude® or DenClude®, for example, contains arginine bicarbonate and calcium carbonate, but not fluoride. The carbonate ion is believed to have cariostatic properties, and the calcium is believed to form in complex with arginine to provide a protective effect. Natural calcium carbonate (chalk), however, has typically a well defined crystal structure (making it very hard) and relatively large particles, as it must be milled to size. It can be highly abrasive, making such a calcium carbonate product less desirable for persons having sensitive teeth.

Accordingly, there is a need for a stable oral care product that provides a basic amino acid and beneficial minerals such as fluoride and calcium, while still maintaining a low radioactive dentin abrasion value (RDA) and providing optimal protection for patients suffering from hypersensitive teeth.

BRIEF SUMMARY OF THE INVENTION

It is now discovered that the benefit of the basic amino acid, e.g., arginine, in treatment and prophylaxis of sensitive teeth can be greatly enhanced through the addition of small particle materials, which in the presence of the basic amino acid, help block the dentinal microtubules believed to be responsible for dentinal hypersensitivity.

The invention encompasses oral care compositions and methods of using the same that are effective in inhibiting or reducing the accumulation of plaque, reducing levels of acid producing (cariogenic) bacteria, remineralizing teeth, inhibiting or reducing gingivitis, and in particular, reducing dentinal hypersensitivity. The invention also encompasses compositions and methods to clean the oral cavity and provide improved methods of promoting oral health and/or systemic health, including cardiovascular health, e.g., by reducing potential for systemic infection via the oral tissues.

The invention thus comprises an oral care composition (a Composition of the Invention), e.g., a dentifrice, comprising
i. an effective amount of a basic amino acid in free or salt form;
ii. a small particle fraction comprising at least about 5%. e.g., at least about 10 to about 40% of the formulation by weight, wherein the particles have a d50 of less than about 5 μm; and
iii. optionally further comprising an effective amount of a fluoride source, e.g., a soluble fluoride salt.

The small particle fraction may be, for example, an abrasive, e.g., selected from precipitated calcium carbonate and silica and mixtures thereof.

In some embodiments, the compositions may have a low radioactive dentin abrasion value (RDA), e.g., less than about 140, e.g., about 30-about 130, e.g. about 30-about 70.

The composition optionally comprises at least about 5%, e.g., at least about 10%, e.g., at least about 20% of an abrasive having a d50 less than about 5 micrometers, e.g., about 0.5 μm to about 5 μm. e.g., silica having a d50 of about 3 μm to about 4 μm or precipitated calcium carbonate having a d50 of about 0.5 μm to about 3 μm.

For example, in one embodiment, the basic amino acid is in the form of arginine bicarbonate, the fluoride is sodium monofluorophosphate, and the abrasive comprises precipitated calcium carbonate. In another embodiment, the basic amino acid is arginine bicarbonate, the fluoride is sodium monofluorophosphate, and the abrasive comprises silica.

In some embodiments, the formulation further comprises an anionic surfactant, e.g., sodium lauryl sulfate; an anionic polymer, e.g., a copolymer of methyl vinyl ether and maleic anhydride; and/or an antibacterial agent, e.g., triclosan.

In particular embodiments, the Compositions of the Invention are in the form of a dentifrice comprising additional ingredients selected from one or more of water, abrasives, surfactants, foaming agents, vitamins, polymers, enzymes, humectants, thickeners, antimicrobial agents, preservatives, flavorings, colorings and/or combinations thereof.

Without intending to be bound by a particular theory, it is believed that the presence of small particles in a formulation with arginine and calcium may help plug the microtubules responsible for hypersensitive teeth and help repair precarious lesions in the enamel and dentin.

In one embodiment precipitated calcium carbonate is generally preferred to natural calcium carbonate. Without intending to be bound by a particular theory, it is hypothesized that natural calcium carbonate has a highly crystalline structure, making it very hard, whereas precipitated calcium carbonate is amorphous and more friable, therefore having a lower abrasivity, while still maintaining adequate cleaning power.

It is moreover surprisingly found that the combination of fluoride and a basic amino acid, e.g., arginine, in an oral care product according to particular embodiments of the present invention produces unexpected benefits beyond and qualitatively different from what can be observed using compositions comprising effective amounts of either compound separately, in promoting remineralization, repairing precarious lesions, and enhancing oral health. It has moreover been found that this action can be further enhanced by addition of a small particle abrasive, which may act to help fill microfissures in the enamel and microtubules in the dentin.

The presence of a basic amino acid is also surprisingly found to reduce bacterial adhesion to the tooth surface, particularly when the basic amino acid is provided in combination with an anionic surfactant. The combination of the basic amino acid and the anionic surfactant and/or anionic polymer e.g., PVM/MA also enhances delivery of antimicrobial agents, particularly triclosan.

The invention thus further encompasses methods to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH about 5.5 following sugar challenge, (xi) reduce plaque accumulation, (xii) reduce dry mouth, (xiii) reduce erosion, (xiv) whiten the teeth, (xv) immunize or protect the teeth against cariogenic bacteria, (xvi) clean the teeth and oral cavity and/or (xvii) promote systemic health, including cardiovascular health, e.g., by reducing potential for systemic infection via the oral tissues, comprising applying a Composition of the Invention to the oral cavity, e.g., by applying a Composition of the Invention to the oral cavity of a subject in need thereof.

DETAILED DESCRIPTION OF THE INVENTION

General Description

The invention thus comprises an oral care composition (Composition 1.0) comprising
i. an effective amount of a basic amino acid in free or salt form,
ii. a small particle fraction comprising at least about 5%, e.g. at least about 20% of the formulation by weight, wherein the particles have a d50 of less than about 5 µm; and
optionally further comprising an effective amount of a fluoride source, e.g., a soluble fluoride salt; for example any of the following compositions:
1.0.1. Composition 1.0 wherein the basic amino acid is arginine, lysine, citrulline, ornithine, creatine, histidine, diaminobutanoic acid, diaminoproprionic acid, salts thereof and/or combinations thereof.
1.0.2. Composition 1.0 or 1.0.1 wherein the basic amino acid has the L-configuration.
1.0.3. Any of the preceding compositions is provided in the form of a salt of a di- or tri-peptide comprising the basic amino acid.
1.0.4. Any of the preceding compositions wherein the basic amino acid is arginine, e.g., L-arginine.
1.0.5. Any of the preceding compositions wherein the basic amino acid is partially or wholly in salt form.
1.0.6. Any of the preceding compositions wherein the basic amino acid comprises arginine phosphate.
1.0.7. Any of the preceding compositions wherein the basic amino acid comprises arginine hydrochloride.
1.0.8. Any of the preceding compositions wherein the basic amino acid comprises arginine sulfate.
1.0.9. Any of the preceding compositions wherein the basic amino acid comprises arginine bicarbonate.
1.0.10. Any of the preceding compositions wherein the salt of the basic amino acid is formed in situ in the formulation by neutralization of the basic amino acid with an acid or a salt of an acid.
1.0.11. Any of the preceding compositions wherein the salt of the basic amino acid is formed by neutralization of the basic amino acid to form a premix prior to combination with the fluoride salt.
1.0.12. Any of the preceding compositions wherein the basic amino acid is present in an amount corresponding to about 0.1 wt. % to about 15 wt. %, e.g. about 1% to about 10%, e.g., about 3% to about 10% of the total composition weight, the weight of the basic amino acid being calculated as free base form.
1.0.13. Composition 1.0.11 wherein the basic amino acid is present in an amount of about 7.5 wt. % of the total composition weight.
1.0.14. Composition 1.0.11 wherein the basic amino acid is present in an amount of about 5 wt. % of the total composition weight.
1.0.15. Composition 1.0.11 wherein the basic amino acid is present in an amount of about 3.75 wt. % of the total composition weight.
1.0.16. Composition 1.0.11 wherein the basic amino acid is present in an amount of about 1.5 wt. % of the total composition weight.
1.0.17. Any of the preceding compositions wherein the fluoride salt is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.0.18. Any of the preceding compositions wherein the fluoride salt is a fluorophosphate.
1.0.19. Any of the preceding composition wherein the fluoride salt is sodium monofluorophosphate.
1.0.20. Any of the preceding compositions wherein the fluoride salt is present in an amount of about 0.01 wt. % to about 2 wt. % of the total composition weight.
1.0.21. Any of the preceding compositions wherein the fluoride salt provides fluoride ion in an amount of about 0.1 to about 0.2 wt. % of the total composition weight.
1.0.22. Any of the preceding compositions wherein the soluble fluoride salt provides fluoride ion in an amount of from about 50 to about 25,000 ppm.
1.0.23. Any of the preceding compositions which is a mouthwash having 100 to about 250 ppm available fluoride ion.
1.0.24. Any of which is a dentifrice having about 750 to about 2000 ppm available fluoride ion.
1.0.25. Any of the preceding compositions wherein the composition comprises about 750 to about 2000 ppm fluoride ion.
1.0.26. Any of the preceding compositions wherein the composition comprises about 1000 to about 1500 ppm fluoride ion.
1.0.27. Any of the preceding compositions wherein the composition comprises about 1450 ppm fluoride ion.
1.0.28. Any of the preceding compositions wherein the pH is between about 6 and about 9, e.g., about 6.5-about 7.4 or about 7.5-about 9.
1.0.29. Any of the preceding compositions wherein the pH is between about 6.5 and about 7.4.
1.0.30. Any of the preceding compositions wherein the pH is approximately neutral.
1.0.31. Any of the preceding compositions wherein the pH is about 8.5-about 9.5.
1.0.32. Any of the preceding compositions further comprising an abrasive or particulate.
1.0.33. The immediately preceding composition wherein the abrasive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof.
1.0.34. The immediately preceding composition wherein the abrasive is selected from a calcium phosphate (e.g., dicalcium phosphate dihydrate), calcium sulfate, precipitated calcium carbonate, silica (e.g., hydrated silica), calcium pyrophosphate and combinations thereof.

1.0.35. Any of the preceding compositions comprising an abrasive in an amount of about 15 wt. % to about 70 wt. % of the total composition weight.

1.0.36. Any of the preceding compositions comprising a small particle abrasive fraction of at least about 5% having a d50 of less than about 5 µm.

1.0.37. Any of the preceding compositions having a RDA of less than about 150.

1.0.38. Any of the preceding compositions having a RDA of about 30-about 130.

1.0.39. Any of the preceding compositions having a RDA of about 30-about 70.

1.0.40. Any of the preceding compositions comprising at least about 5% small particle synthetic amorphous silica (d50 about 3-about 4 um).

1.0.41. Any of the preceding compositions comprising at least about 20% small particle precipitated calcium carbonate (d50 about 0.5-about 3 um).

1.0.42. Any of the preceding compositions further comprising an anti-calculus agent.

1.0.43. Any of the preceding compositions further comprising an anti-calculus agent which is a polyphosphate, e.g., pyrophosphate, tripolyphosphate, or hexametaphosphate, e.g., in sodium salt form.

1.0.44. Any of the preceding compositions comprising at least one surfactant.

1.0.45. Any of the preceding compositions comprising at least one surfactant selected from sodium lauryl sulfate, cocamidopropyl betaine, and combinations thereof.

1.0.46. Any of the preceding compositions comprising an anionic surfactant.

1.0.47. Any of the preceding compositions comprising sodium lauryl sulfate.

1.0.48. Any of the preceding compositions comprising at least one humectant.

1.0.49. Any of the preceding compositions comprising at least one humectant selected from glycerin, sorbitol and combinations thereof.

1.0.50. Any of the preceding compositions comprising at least one polymer.

1.0.51. Any of the preceding compositions comprising at least one polymer selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof.

1.0.52. Any of the preceding compositions comprising gum strips or fragments.

1.0.53. Any of the preceding compositions comprising flavoring, fragrance and/or coloring.

1.0.54. Any of the preceding compositions comprising water.

1.0.55. Any of the preceding compositions comprising an antibacterial agent.

1.0.56. Any of the preceding compositions comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigal locatechin gal late, epigallocatechin, gallic acid, miswak extract, sea-buckthorn extract), bisguanide antiseptics (e.g., chlorhexidine, alexidine or octenidine), quaternary ammonium compounds (e.g. cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.0.57. Any of the preceding compositions comprising an anti-inflammatory compound, e.g., an inhibitor of at least one of host pro-inflammatory factors selected from matrix metalloproteinases (MMP's), cyclooxygenases (COX), $PGE_2$, interleukin 1 (IL-1), IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK), e.g., selected from aspirin, ketorolac, flurbiprofen, ibuprofen, naproxen, indomethacin, aspirin, ketoprofen, piroxicam, meclofenamic acid, nordihydroguaiaretic acid, and mixtures thereof.

1.0.58. Any of the preceding compositions comprising an antioxidant, e.g., selected from the group consisting of Co-enzyme Q10, PQQ, Vitamin C, Vitamin E, Vitamin A, anethole-dithiothione, and mixtures thereof.

1.0.59. Any of the preceding compositions comprising triclosan.

1.0.60. Any of the preceding compositions comprising an antibacterial agent in an amount of about 0.01-about 5 wt. % of the total composition weight.

1.0.61. Any of the preceding compositions comprising triclosan in an amount of about 0.01 to about 1 wt. percent of the total composition weight.

1.0.62. Any of the preceding compositions comprising triclosan in an amount of about 0.3% of the total composition weight.

1.0.63. Any of the preceding compositions comprising triclosan and $Zn^{2+}$ ion source e.g., zinc citrate.

1.0.64. Any of the preceding compositions comprising a whitening agent.

1.0.65. Any of the preceding compositions comprising a whitening agent selected from a whitening active selected from the group consisting of peroxides, metal chlorites, perborates, percarbonates, peroxyacids, hypochlorites, and combinations thereof 1.0.66. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.0.67. Any of the preceding compositions further comprising a source of calcium and phosphate selected from (i) calcium-glass complexes, e.g., calcium sodium phosphosilicates, and (ii) calcium-protein complexes. e.g., casein phosphopeptide-amorphous calcium phosphate.

1.0.68. Any of the preceding compositions further comprising a soluble calcium salt, e.g., selected from calcium sulfate, calcium chloride, calcium nitrate, calcium acetate, calcium lactate, and combinations thereof.

1.0.69. Any of the preceding compositions further comprising an agent that interferes with or prevents bacterial attachment, e.g., solbrol or chitosan.

1.0.70. Any of the preceding compositions further comprising a physiologically acceptable potassium salt, e.g., potassium nitrate, potassium citrate, or potassium chloride, in an amount effective to reduce dentinal sensitivity.

1.0.71. Any of the preceding compositions comprising from about 0.1% to about 7.5% of a physiologically acceptable potassium salt, e.g., potassium nitrate and/or potassium chloride.

1.0.72. Any of the preceding compositions wherein the salt of a basic amino acid is arginine bicarbonate, the fluoride is sodium monofluorophosphate, and the abrasive is precipitated calcium carbonate.

1.0.73. Any of the preceding compositions wherein the salt of a basic amino acid is arginine bicarbonate, the fluoride is sodium monofluorophosphate, and the abrasive is silica.

1.0.74. Any of the preceding compositions effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) reduce dry mouth, (xiii) clean the teeth and oral cavity (xiv) reduce erosion, (xv) whiten teeth, and/or (xvi) immunize the teeth against cariogenic bacteria.

1.0.75. A composition obtained or obtainable by combining the ingredients as set forth in any of the preceding compositions.

1.0.76. Any of the preceding compositions in a form selected from mouthrinse, toothpaste, tooth gel, tooth powder, non-abrasive gel, mousse, foam, mouth spray, lozenge, oral tablet, dental implement, and pet care product.

1.0.77. Any of the preceding compositions wherein the composition is toothpaste.

1.0.78. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.0.79. Any of the preceding compositions 1.0-1.0.76 wherein the composition is a mouthwash.

In another embodiment, the invention encompasses a Composition of the Invention (Composition 1.1), e.g., according to any of the preceding Compositions 1.0-1.0.79, comprising
i. an effective amount of a basic amino acid in free or salt form;
ii. an effective amount of a fluoride source, e.g., soluble fluoride salt;
iii. an anionic surfactant. e.g., sodium lauryl sulfate.

In another embodiment, the invention encompasses a Composition of the Invention (Composition 1.2) e.g., according to any of the preceding Compositions 1.0-1.0.79, comprising
i. an effective amount of a basic amino acid in free or salt form;
ii. an effective amount of a fluoride source, e.g., soluble fluoride salt;
iii. an anionic surfactant. e.g., sodium lauryl sulfate;
iv. an anionic polymer, e.g., a copolymer of methyl vinyl ether and maleic anhydride; and
v. an antibacterial agent, e.g. triclosan.

In another embodiment, the invention encompasses a Composition of the Invention (Composition 1.3) e.g., according to any of the preceding Compositions 1.0-1.0.79, comprising
i. an effective amount of a basic amino acid in free or salt form,
ii. an effective amount of a fluoride source, e.g., a soluble fluoride salt; and
iii. small particle abrasive having a RDA of less than about 160, e.g., about 30-about 130, e.g., comprising at least about 5% of an abrasive having a d50 less than about 5 micrometers. e.g., silica having a d50 of about 3-about 4 μm or precipitated calcium carbonate having a d50 of about 0.5-about 3 μm.

In another embodiment, the invention encompasses a method ((Method 2) to improve oral health comprising applying an effective amount of the oral composition of any of the embodiments under Compositions 1.0, 1.1, 1.2, 1.3 or 1.4. to the oral cavity of a subject in need thereof, e.g., a method to
i. reduce or inhibit formation of dental caries,
ii. reduce, repair or inhibit pre-carious lesions of the enamel, e.g., as detected by quantitative light-induced fluorescence (QLF) or electrical caries measurement (ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. reduce levels of acid producing bacteria,
viii. to increase relative levels of arginolytic bacteria,
ix. inhibit microbial biofilm formation in the oral cavity,
x. raise and/or maintain plaque pH at levels of at least pH about 5.5 following sugar challenge,
xi. reduce plaque accumulation.
xii. reduce erosion,
xiii. whiten teeth.
xiv. enhance systemic health,
xv. immunize or protect teeth against cariogenic bacteria; and/or clean the teeth and oral cavity.

The invention further comprises the use of arginine in the manufacture of a Composition of the Invention, e.g., for use in any of the indications set forth in Method 2.

The invention further provides an oral care composition comprising a basic amino acid, in free or salt form, and an abrasive material, the abrasive material including a small particle fraction comprising at least about 5 wt % of the total composition weight, wherein the particles of the small particle fraction have a d50 of less than 5 μm, for use in the treatment of sensitive teeth within an oral cavity of a subject. It has been found surprisingly that such a composition, including the combination of the basic amino acid and the small particle fraction of abrasive, exhibits enhanced dentinal occlusion of the teeth.

The invention further provides an oral care composition comprising a basic amino acid, in free or salt form, and a small particle fraction comprising at least about 5% of the composition by weight, wherein the particles of the small particle fraction have a d50 of less than about 5 μm, for enhancing dentinal occlusion within an oral cavity of a subject.

The invention further provides the use of a basic amino acid, in free or salt form, in an oral care composition comprising a small particle fraction comprising at least about 5% of the composition by weight, wherein the particles of the small particle fraction have a d50 of less than about 5 μm, for enhancing dentinal occlusion within an oral cavity of a subject.

The invention further provides the use of a basic amino acid, in free or salt form, for the manufacture of a medicament which includes a small particle fraction comprising at least about 5% of the medicament by weight, wherein the particles of the small particle fraction have a d50 of less than about 5 μm, for enhancing dentinal occlusion within an oral cavity of a subject.

The invention further provides a method of treating sensitive teeth within an oral cavity, the method comprising treating the oral cavity of a subject with an oral care composition comprising a basic amino acid, in free or salt form, and a small particle fraction comprising at least about 5% of the composition by weight, wherein the particles of the small particle fraction have a d50 of less than about 5 nm, to enhance dentinal occlusion.

It may therefore be seen by the skilled practitioner in the oral care art that a surprising technical effect and advantage of enhanced dentinal occlusion of sensitive teeth can result from the formulation, and use, of an oral care composition, for example a dentifrice, in accordance with one or more aspects of the invention, which are directed to the provision of combinations of active components or ingredients, and preferably their respective amounts, within the composition.

Levels of active ingredients will vary based on the nature of the delivery system and the particular active. For example, the basic amino acid may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride may be present at levels of, e.g., about 25 to about 10,000 ppm, for example about 25 to about 250 ppm for a mouthrinse, about 750 to about 2,000 ppm for a consumer toothpaste, or about 2,000 to about 10,000 ppm for a professional or prescription treatment product. Levels of antibacterial will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of about 7 or greater.

Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acids are selected from arginine, citrulline, and ornithine.

In certain embodiments, the basic amino acid is arginine, for example, l-arginine, or a salt thereof.

In some embodiments the basic amino acid comprises at least one intermediate produced in the arginine deiminase system. The intermediates produced in the arginine deiminase system may be useful in an oral care composition to provide plaque neutralization for caries control and/or prevention. Arginine is a natural basic amino acid that may be found in the oral cavity. Arginine in the mouth may be utilized by certain dental plaque bacterial strains such as S. sanguis, S. gordonii, S. parasanguis, S. rattus, S. milleri, S. anginosus, S. faecalis, A. naeslundii, A. odonolyticus, L. cellobiosus, L. brevis, L. fermentum, P. gingivalis, and T. denticola for their survival. Such organisms may perish in an acidic environment that may be present at areas close to the tooth surface where acidogenic and aciduric cariogenic strains may use sugars to produce organic acids. Thus, these arginolytic strains may break down arginine to ammonia to provide alkalinity to survive and, in addition, buffer the plaque and make a hostile environment for the cariogenic systems.

Such arginolytic organisms may catabolize arginine by an internal cellular enzyme pathway system called the "arginine deiminase system" whereby intermediates in the pathway are formed. In this pathway, L-arginine may be broken down to L-citrulline and ammonia by arginine deiminase. L-citrulline may then be broken down by ornithane trancarbamylase in the presence of inorganic phosphate to L-ornithine and carbamyl phosphate. Carbamate kinase may then break down carbamyl phosphate to form another molecule of ammonia and carbon dioxide, and in the process also forms ATP (adenosine 5'-triphosphate). ATP may be used by the arginolytic bacteria as an energy source for growth. Accordingly, when utilized, the arginine deiminase system may yield two molecules of ammonia.

It has been found that, in some embodiments, the ammonia may help in neutralizing oral plaque pH to control and/or prevent dental caries.

The oral care composition of some embodiments of the present invention may include intermediates produced in the arginine deiminase system. Such intermediates may include citrulline, ornithine, and carbamyl phosphate. In some embodiments, the other care composition includes citrulline. In some embodiments, the oral care composition includes ornithine. In some embodiments, the oral care composition includes carbamyl phosphate. In other embodiments, the oral care composition includes any combination of citrulline, ornithine, carbamyl phosphate, and/or other intermediates produced by the arginine deiminase system.

The oral care composition may include the above described intermediates in an effective amount. In some embodiments, the oral care composition includes about 1 mmol/L to about 10 mmol/L intermediate. In other embodiments, the oral care composition includes about 3 mmol/L to about 7 mmol/L intermediate. In other embodiments, the oral care composition includes about 5 mmol/L intermediate.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In various embodiments, the basic amino acid is present in an amount of about 0.5 wt. % to about 20 wt. % of the total composition weight, about 1 wt. % to about 10 wt. % of the total composition weight, for example about 1.5 wt. %, about 3.75 wt. %, about 5 wt. %, or about 7.5 wt. % of the total composition weight.

RDA:

RDA is an abbreviation for radioactive dentin abrasion, a relative measure of abrasivity. Typically, extracted human or cow teeth are irradiated in a neutron flux, mounted in methylmethacrylate (bone glue), stripped of enamel, inserted into a brushing-machine, brushed by American Dental Association (ADA) standards (reference toothbrush, 150 g pressure, 1500 strokes, 4-to-1 water-toothpaste slurry). The radioactivity of the rinse water is then measured and recorded. For experimental control, the test is repeated with an ADA reference toothpaste made of calcium pyrophosphate, with this measurement given a value of 100 to calibrate the relative scale.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to 25,000 ppm of fluoride ions, generally at least about 500 ppm, e.g., about 500 to about 2000 ppm, e.g., about 1000 to about 1600 ppm, e.g. about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as 5,000 or even 25,000 ppm fluoride.

Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Where the composition comprises calcium bicarbonate sodium monofluorophosphate is preferred to sodium fluoride for stability reasons.

Abrasives

The Compositions of the Invention may comprise a precipitated calcium carbonate (PCC) abrasive, calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. Alternatively, calcium carbonate, and in particular precipitated calcium carbonate, may be employed as an abrasive.

The compositions may include one or more additional abrasives, for example silica abrasives such as precipitated silicas having a mean particle size of up to about 20 µm, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size of about 0.1 and about 30 µm, about 5 and about 15 µm. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 µm to about 12 µm, and about 5 to about 10 µm.

In particular embodiments, the abrasive materials comprise a large fraction of very small particles, e.g., having a d50 less than about 5 µm. For example small particle silica (SPS) having a d50 of about 3-about 4 µm, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 5 to about 25% small particles e.g., SPS and about 10 to about 30% of a conventional abrasive.

Low oil absorption silica abrasives particularly useful in the practice of the invention are marketed under the trade designation Sylodent XWA® by Davison Chemical Division of W.R. Grace & Co. Baltimore, Md. 21203. Sylodent 650 XWA®, a silica hydrogel composed of particles of colloidal silica having a water content of about 29% by weight averaging about 7 to about 10 µm in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

In some embodiments the basic amino acid is incorporated into a dentifrice composition having a base formulation comprising calcium carbonate, and in particular precipitated calcium carbonate, as an abrasive. L-arginine and arginine salts such as arginine bicarbonate are themselves distinctly bitter in taste, and in aqueous solution can also impart a fishy taste. Consequently, it was expected that when L-arginine or arginine salts were incorporated into oral care products such as dentifrice formulations at effective concentrations to impart anticavity efficacy and sensitivity relief, typically in an amount of from 2 to 10 wt % based on the total weight of the dentifrice formulation, the taste and mouthfeel of the dentifrice formulations would be degraded as compared to the same formulation without the addition of L-arginine or arginine salts.

However, it has surprisingly been found in accordance with this aspect of the present invention that the addition of L-arginine or arginine salts to a base dentifrice formulation comprising calcium carbonate can provide a significant enhancement of taste and mouthfeel attributes to the dentifrice formulation and to an increase in the overall acceptance of the product to a consumer.

Agents to Increase the Amount of Foaming

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

In a particular embodiment, the Composition of the Invention comprises an anionic surfactant, e.g., sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvnone, and anethole. Certain embodiments employ the oils of peppermint and spearmint.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

Chelating Agents

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

Polymers

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10.000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000.000, described in U.S. Pat. No. 4,842,847. Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

Water

Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerin and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Methods of Manufacture

The compositions of the present invention can be made using methods which are common in the oral product area.

In one illustrative embodiment, the oral care composition is made by neutralizing or partially neutralizing arginine in a gel phase with an acid, e.g., phosphoric acid, hydrochloric acid or carbonic acid, and mixing to form Premix 1.

Actives such as, for example, vitamins. CPC, fluoride, abrasives, and any other desired active ingredients are added to Premix 1 and mixed to form Premix 2.

Where the final product is a toothpaste, a toothpaste base, for example, dicalcium phosphate, precipitated calcium carbonate, and/or silica, is added to Premix 2 and mixed. The final slurry is formed into an oral care product.

Composition Use

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit pre-carious lesions of the enamel, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery, or soft. In this type of study, typically the results are reported as electrical resistance (higher number is better) for the ECM measurements and an improvement in hardness of the lesion based on the tactile probe score.

The Compositions of the Invention are thus useful in a method to reduce pre-carious lesions of the enamel (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least pH 5.5 following sugar challenge, reduce plaque accumulation, and/or clean the teeth and oral cavity.

Finally, by increasing the pH in the mouth and discouraging pathogenic bacteria, the Compositions of the Invention are useful to promote healing of sores or cuts in the mouth.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to *Heliobacter*, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

The compositions and methods according to the invention can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

RDA Test of Arginine Calcium Carbonate Formulation

Natural calcium carbonate formulations show high RDA:
Formulation A: Prophylactic paste:
 31% Sylodent 756.
 15% Vicron 25-11 (fine ground CaCO$_3$, natural source),
 14% Vicron 41-8 (fine ground CaCO$_3$).
 10% Arginine Bicarbonate
 RDA: 230
Formulation B: Consumer sensitivity dentifrice
 50% Vicron 25-11 (fine ground CaCO$_3$),
 7%, Sylodent 15,
 2% Arginine Bicarbonate
 RDA: 179

Example 2

Low RDA Formulations

Precipitated calcium carbonate (PCC) formulations show lower RDA:

| RAW MATERIAL | WEIGHT % |
|---|---|
| Deionized Water | 30.260 |
| Sorbitol 70% | 23.000 |
| Carboxymethyl cellulose | 0.940 |
| Xanthan gum | 0.210 |
| Sodium Saccharin | 0.450 |
| Sodium | 1.100 |
| Sodium bicarbonate | 0.500 |
| N-Silicate (1:3.26, 41 BE) | 0.800 |
| L-Arginine bicarbonate | 5.000 |
| Precipitated calcium | 35.000 |
| Sodium lauryl sulfate | 1.620 |
| Methyl-P-hydroxybenzoate | 0.100 |
| Propyl-P-hydroxybenzoate | 0.020 |
| Flavor | 1.000 |
| TOTAL | 100.000 |
| RDA | 107 |

Example 3

Low RDA Formula with Small Particle PCC Abrasive

| RAW MATERIAL | WEIGHT % |
|---|---|
| Deionized Water | 25.660 |
| Sorbitol 70% | 23.000 |
| Carboxymethyl cellulose | 0.800 |
| Xanthan gum | 0.150 |
| Sodium Sacharin | 0.250 |
| Sodium Monofluorophosphate | 1.100 |
| Sodium bicarbonate | 0.500 |
| N-Silicate (1:3.26, 41 BE) | 0.800 |
| L-Arginine bicarbonate | 10.000 |
| Precipitated calcium carbonate | 10.000 |
| Small particle size - Precipitated calcium carbonate | 25.000 |
| Sodium lauryl sulfate | 1.620 |
| Methyl-P-hydroxybenzoate | 0.100 |
| Propyl-P-hydroxybenzoate | 0.020 |
| Flavor | 1.000 |
| TOTAL | 100.000 |
| RDA | 52 |

Example 4

Small Particle Silica Formulations

Prototypes are made with incorporation of 5% and 10% small particle silica (d50 3-4 micron, Sorbosil AC43 from Ineos) in PCC base dentifrice w/5% arginine bicarbonate. Dentine disks are brushed with dentifrice prototypes in order to mimic three day brushing regimen, or 6 treatments. Confocal microscopy images are taken at three stages: prior treatment (baseline), after dentifrice treatment and after acid challenge.

Formulations containing small particle silica show better performance after acid challenge in comparison to control dentifrice.

TABLE 1

Examples of dentifrice formulation:

| Ingredient | Formula I | Formula II | Formula III | Formula IV | Formula V |
|---|---|---|---|---|---|
| Sorbitol | 22.25 | 22.25 | 22.25 | 22.25 | 22.25 |
| Sodium CMC | 1.00 | 1.00 | 1.00 | 1.00 | 1.00 |
| Xanthan gum | 0.25 | 0.25 | 0.25 | 0.25 | 0.25 |
| Sodium Monofluorophosphate | 1.10 | 1.10 | 1.10 | 1.10 | 1.10 |
| Sodium Saccharin | 0.50 | 0.50 | 0.50 | 0.50 | 0.50 |
| Sodium Hydroxide | 0.50 | 0.50 | 0.50 | 0.50 | 0.50 |
| Arginine Bicarbonate | 5.00 | 5.00 | 5.00 | 5.00 | 5.00 |
| Sodium Bicarbonate | 0.50 | 0.50 | 0.50 | 0.50 | 0.50 |
| Precipitated calcium carbonate | 34.00 | 34.00 | 34.00 | 29.00 | 29.00 |
| Synthetic amorphous silica (d50 3-4 um) | — | 5.00 | 10.00 | 5.00 | 10.00 |
| Potassium nitrate | — | — | — | 5.00 | 5.00 |
| Sodium lauryl sulfate | 1.50 | 1.50 | 1.50 | 1.50 | 1.50 |
| Flavor | 1.00 | 1.00 | 1.00 | 1.00 | 1.00 |
| Water (to balance) | QS | QS | QS | QS | QS |

Dentin Disk Preparation
 1. Dentin disks are cut from extracted human teeth.
 2. Dentin disks are then sanded with 600 grit paper and polished on magnification side. Disks are placed into fresh PBS solution.
 3. Using tweezers, dentin disk is suspended in 30 ml of 6% citric acid for 1 minute, then disk rinsed with PBS.
 4. Dentin disk placed in 60 ml DI water and sonicated for 60 minutes. Clean disks put in PBS for storage.
 5. Baseline readings taken on Confocal microscope—each cell in duplicate.

Treatment
1. Dip toothbrush into beaker containing Deionized water. Then, with a 1 inch ribbon of dentifrice, brush dentin disk in one direction for 45 seconds. Rinse with PBS and agitate for 1 hour in PBS, repeating brushing to 6 treatments, then measure on Confocal.
2. Coke Acid Challenge: Dentin disk is suspended with tweezers for 1 minute in Coke Classic Soda, then rinsed with PBS and then with DI water. Place in PBS for storage prior to measurements.

Three dentifrices are tested in vitro for dentinal occlusion efficacy: formulas I, II and III (table 1). Confocal images are taken of baseline, after 6 brushings and after acid challenge. The brushing treatments results in increasing dentinal occlusion with addition of small particle silica (SPS). The sample with no addition of SPS (Formula I, control) shows only modest occlusion after 6 treatments, in comparison to 5% and 10% SPS.

Example 5

Dentifrice Formulation Comprising Precipitated Calcium Carbonate (PCC)

A panel of consumer testers trained in testing the sensory attributes of dentifrice formulations was subjected to different dentifrice formulations which were used under double-blind consumer testing conditions replicating consumer use of dentifrice formulations.

The panel was asked to use the dentifrice formulations conventionally and then to rate various sensory characteristics. For a base dentifrice formulation comprising precipitated calcium carbonate (PCC), the known formulation acted as a placebo control, and corresponding formulations additionally comprising 1, 2, 3 or 5 wt % arginine bicarbonate were also tested. Surprisingly, it was found that the arginine bicarbonate-containing PCC formulations exhibited increases in consumer acceptance for flavor intensity, cooling and ease to foam attributes, and moreover the formulation additionally comprising 2 wt % arginine bicarbonate exhibited increases in overall liking, overall liking of taste, taste while brushing and taste after brushing. In addition, the formulations additionally comprising arginine bicarbonate were perceived as significantly better than the placebo control in all image attributes, including perceived efficacy, mouth/teeth feeling of clean, product suitability, taste and overall product quality.

In contrast, when formulations having dicalcium phosphate, rather than precipitated calcium carbonate (PCC), as the base were tested, the addition of arginine bicarbonate did not exhibit significantly improved sensory characteristics as compared to the same formulation without the addition of arginine bicarbonate.

The Example shows that the addition of a basic amino acid such as arginine, in particular as bicarbonate, can surprisingly enhance the sensory characteristics of dentifrice formulations, most particularly having a base formulation of precipitated calcium carbonate (PCC), when used in an oral care composition of the invention.

Example 6

Basic Amino Acids Other than Arginine

An overnight culture of *S. sanguis* was grown at 37° C. in trypticase soy broth (Becton Dickinson, Sparks, Md.). The culture was centrifuged at 5,000 rpm for 5 minutes at 1 milliliter at a time into preweighed tubes in order to accumulate approximately 5 milligrams of wet pellet weight. The pellet was then resuspended into 20 millimolar potassium phosphate buffer (J T Baker, Phillipsburg, N.J.), pH 4.0, to simulate a stressed environment for the bacterial cell where ammonia would be produced for survival. The final concentration was 5 milligram per milliliter. To this final concentration, a 5 millimolar final concentration of L-arginine, L-citrulline, or L-ornithine was added along with a 0.1% final concentration of sucrose (VWR, West Chester, Pa.). This mixture was then incubated at 37° C. in a shaking water bath for 30 minutes before ammonia production was determined.

In order to analyze for ammonia, an Ammonia Assay kit was used from Diagnostic Chemicals Limited (Oxford, Conn.). The intended use of this specific kit is for the in vitro quantification of ammonia in plasma, but the procedure was modified in order to determine and quantify the ammonia production in plaque and/or bacteria.

The table below shows the ammonia production values from 6 separate trials using *S. sanguis* at pH 4.0 as described above. The results confirm that the intermediates produced by the arginine deiminase system can be used to produce ammonia for cell survival.

| Trial # | L-Arginine Ammonia (ppm) | L-Citrulline Ammonia (ppm) | L-Ornithine Ammonia (ppm) |
| --- | --- | --- | --- |
| 1 | 0.509 | 0.185 | 0.185 |
| 2 | 0.866 | 0.346 | 0.260 |
| 3 | 2.20 | 0.332 | 0.047 |
| 4 | 1.62 | 0.194 | 0.0 |
| 5 | 0.5 | 0.226 | 0.181 |
| 6 | 0.679 | 0.951 | 0.135 |
| Mean | 1.06 | 0.951 | 0.134 |

The Example shows that basic amino acids other than arginine are effective to produce ammonia within the oral cavity, and thus to increase plaque pH when used in a oral care composition of the invention.

The invention claimed is:

1. An oral care composition comprising a. an effective amount of a basic amino acid in free or salt form; and b. a small particle fraction comprising at least about 5% of the composition by weight, wherein particles of the small particle fraction have a d50 of less than about 5 μm and wherein the small particle fraction comprises precipitated calcium carbonate having d50 of about 0.5 to about 4 μm and silica having d50 of about 1 to about 4 μm.

2. A composition according to claim 1 further comprising an effective amount of a soluble fluoride salt.

3. A composition according to claim 1 wherein the basic amino acid is arginine.

4. A composition according to claim 1 wherein the basic amino acid is partially or wholly in salt form selected from arginine bicarbonate, arginine hydrochloride, arginine phosphate, and combinations thereof.

5. A composition according to claim 1 comprising arginine bicarbonate.

6. A composition according to claim 1, having a radioactive dentin abrasion (RDA) of about 30-about 130.

7. A composition according to claim 1, having a radioactive dentin abrasion (RDA) of about 30-about 70.

8. A composition according to claim 1, comprising at least about 20% of small particles having a d50 less than about 5 μm.

9. A composition according to claim 1, wherein the basic amino acid is arginine bicarbonate and which further comprises sodium monofluorophosphate.

10. A composition according to claim 1, further comprising an anionic surfactant.

11. A composition according to claim 10 wherein the anionic surfactant is sodium lauryl sulfate.

12. A composition according to claim 1 further comprising an antibacterial agent.

13. A composition according to claim 12 wherein the antibacterial agent is triclosan.

14. A composition according to claim 1 further comprising an anionic polymer.

15. A composition according to claim 14 wherein the anionic polymer is a copolymer of methyl vinyl ether and maleic anhydride.

16. The composition according to claim 1, in the form of a toothpaste further comprising one or more of water, abrasives, surfactants, foaming agents, vitamins, polymers, enzymes, humectants, thickeners antimicrobial agents, preservatives, flavorings, colorings and/or combinations thereof.

17. A method comprising applying an effective amount of the oral care composition of claim 1 to an oral cavity of a subject in need thereof, to reduce or inhibit formation of dental caries; to reduce, repair or inhibit pre-carious lesions of enamel; to reduce or inhibit demineralization and promote remineralization of teeth; to reduce hypersensitivity of teeth; to reduce or inhibit gingivitis; to promote healing of sores or cuts in a mouth; to reduce levels of acid producing bacteria; to increase relative levels of arginolytic bacteria; to inhibit microbial biofilm formation in the oral cavity; to raise and/or maintain plaque pH at levels of at least pH 5.5 following sugar challenge; to reduce plaque accumulation; to treat, reduce, relieve or alleviate dry mouth; to whiten teeth; to reduce erosion; to improve systemic health; to immunize teeth against cariogenic bacteria; and/or to clean teeth and oral cavity.

18. The method of claim 17 to reduce hypersensitivity of the teeth.

19. An oral care composition comprising a basic amino acid, in free or salt form, and an abrasive material, the abrasive material including a small particle fraction comprising at least about 5 wt % of the total composition weight, wherein particles of the small particle fraction have a d50 of less than 5 μm, and wherein the small particle fraction comprises precipitated calcium carbonate having d50 of about 0.5 to about 4 μm and silica having d50 of about 1 to about 4 μm, for use in the treatment of sensitive teeth within an oral cavity of a subject.

20. An oral care composition according to claim 19 wherein the basic amino acid is present in an amount of from 0.1 to 20 wt % of the total composition weight.

21. An oral care composition according to claim 19 wherein the basic amino acid is present in an amount of from 1 to 10 wt % of the total composition weight.

22. An oral care composition according to claim 19 wherein the basic amino acid comprises arginine.

23. An oral care composition according to claim 19 further comprising an antibacterial agent in an amount of from 0.01 to 5 wt % of the total composition weight.

24. An oral care composition according to claim 23 wherein the antibacterial agent is present in an amount of from 0.01 to 1 wt % of the total composition weight.

25. An oral care composition according to claim 23 wherein the antibacterial agent is triclosan.

26. An oral care composition according to claim 19 further comprising a soluble fluoride salt in an amount of from 0.01 to 2 wt % of the total composition weight.

27. An oral care composition according to claim 19 further comprising a source of fluoride ions in an amount to provide 50 to 25,000 ppm by weight of fluoride ions in the total composition weight.

28. An oral care composition according to claim 26 wherein the soluble fluoride salt is selected from sodium fluoride, sodium monofluorophosphate, and mixtures thereof.

29. An oral care composition according to claim 19 further comprising an anionic surfactant in an amount of from 0.01 to 10 wt % of the total composition weight.

30. An oral care composition according to claim 29 wherein the anionic surfactant is present in an amount of from 0.3 to 4.5 wt % of the total composition weight.

31. An oral care composition according to claim 29 wherein the anionic surfactant is selected from sodium lauryl sulfate, sodium laureth sulfate, and mixtures thereof.

32. An oral care composition according to claim 19 wherein the small particle fraction comprises at least about 20 wt % of the total composition weight.

33. An oral care composition according to claim 32 wherein the abrasive material comprises from 15 to 70 wt % of the total composition weight.

34. An oral care composition comprising a basic amino acid, in free or salt form, and a small particle fraction of an abrasive material comprising at least about 5% of the composition by weight, wherein particles of the small particle fraction have a d50 of less than about 5 μm, and wherein the small particle fraction comprises precipitated calcium carbonate having d50 of about 0.5 to about 4 μm and silica having d50 of about 1 to about 4 μm, for enhancing dentinal occlusion within an oral cavity of a subject.

35. An oral care composition according to claim 34 wherein the basic amino acid comprises arginine and is present in an amount of from 0.1 to 20 wt % of the total composition weight.

36. An oral care composition according to claim 34 further comprising an antibacterial agent comprising triclosan in an amount of from 0.01 to 5 wt % of the total composition weight.

37. An oral care composition according to claim 34 further comprising a soluble fluoride salt in an amount of from 0.01 to 2 wt % of the total composition weight.

38. An oral care composition according to claim 34 further comprising a source of fluoride ions in an amount to provide 50 to 25,000 ppm by weight of fluoride ions in the total composition weight.

39. An oral care composition according to claim 34 further comprising an anionic surfactant in an amount of from 0.01 to 10 wt % of the total composition weight, the anionic surfactant being selected from sodium lauryl sulfate, sodium laureth sulfate, and mixtures thereof.

40. An oral care composition according to claim 34 wherein the small particle fraction comprises at least about 20 wt % of the total composition weight.

41. An oral care composition according to claim 34 wherein the abrasive material comprises from 15 to 70 wt % of the total composition weight.

42. A method of treating sensitive teeth within an oral cavity, the method comprising applying to the oral cavity of a subject the oral care composition of claim 1 comprising a basic amino acid, in free or salt form, and a small particle fraction comprising at least about 5% of the composition by weight, wherein the particles of the small particle fraction have a d50 of less than about 5 μm, and wherein the small particle fraction comprises precipitated calcium carbonate having d50 of about 0.5 to about 4 μm and silica having d50 of about 1 to about 4 μm, to enhance dentinal occlusion.

43. A composition according to claim 12, wherein the antibacterial agent is a zinc salt.

44. A composition according to claim 43, wherein the zinc salt is zinc citrate.

45. A composition according to claim 19 further comprising a zinc salt.

46. A composition according to claim 45, wherein the zinc salt is zinc citrate.

47. A composition according to claim 34 further comprising a zinc salt.

48. A composition according to claim 47, wherein the zinc salt is zinc citrate.

* * * * *